United States Patent [19]
Erades et al.

[11] Patent Number: 5,820,571
[45] Date of Patent: Oct. 13, 1998

[54] MEDICAL BACKLOADING WIRE

[75] Inventors: Pierre Erades, Momtingy le Bretonneux, France; Richard A. Gambale, Tyngsboro, Mass.; Tomas Raymond Anthony, Kilkenny, Ireland

[73] Assignee: C. R. Bard, Inc., Murray Hill, N.J.

[21] Appl. No.: 667,943

[22] Filed: Jun. 24, 1996

[51] Int. Cl.[6] .................................................. A61M 25/01
[52] U.S. Cl. ............................................ 600/585; 600/434
[58] Field of Search .................................. 128/772, 657, 128/658; 604/170, 171, 164; 600/585, 434, 435

[56] References Cited

U.S. PATENT DOCUMENTS

| | | | |
|---|---|---|---|
| Re. 34,466 | 12/1993 | Taylor et al. .......................... | 128/772 |
| 4,659,328 | 4/1987 | Potter et al. . | |
| 4,827,941 | 5/1989 | Taylor et al. . | |
| 4,958,642 | 9/1990 | Christian et al. . | |
| 4,961,433 | 10/1990 | Christian . | |
| 4,991,602 | 2/1991 | Amplatz et al. ........................ | 128/772 |
| 5,109,867 | 5/1992 | Twyford, Jr. . | |
| 5,113,872 | 5/1992 | Jahrmarkt et al. . | |
| 5,133,364 | 7/1992 | Palermo et al. . | |
| 5,188,621 | 2/1993 | Samson . | |
| 5,267,573 | 12/1993 | Evans et al. . | |
| 5,271,415 | 12/1993 | Foerster et al. . | |
| 5,275,173 | 1/1994 | Samson et al. . | |
| 5,327,885 | 7/1994 | Griffith . | |
| 5,357,978 | 10/1994 | Turk . | |
| 5,363,847 | 11/1994 | Viera ...................................... | 128/657 |
| 5,365,943 | 11/1994 | Jansen . | |
| 5,404,888 | 4/1995 | Kontos et al. . | |
| 5,415,178 | 5/1995 | Hsi et al. . | |
| 5,497,782 | 3/1996 | Fugoso . | |
| 5,507,729 | 4/1996 | Lindenberg et al. .................. | 128/772 |

FOREIGN PATENT DOCUMENTS 0591945  4/1994  European Pat. Off. .

*Primary Examiner*—William E. Kamm
*Assistant Examiner*—Carl H. Layno
*Attorney, Agent, or Firm*—Arthur Z. Bookstein; John F. Perullo

[57] ABSTRACT

A short backloading wire is provided to facilitate the backloading of a catheter onto a guidewire that has a tubular connector. This backloading wire is preferably shorter than the guidewire and at least one end is engageable with the hypotube connector at the proximal end of many guidewires. The free end of the backloading wire has a reduced diameter making easier to insert into the distal tip of a catheter during backloading.

32 Claims, 3 Drawing Sheets

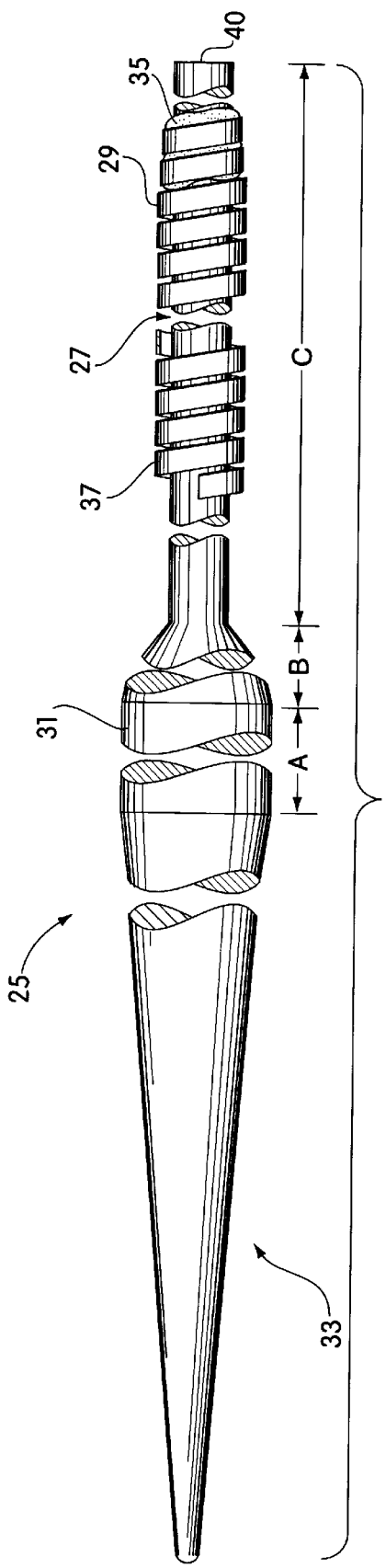
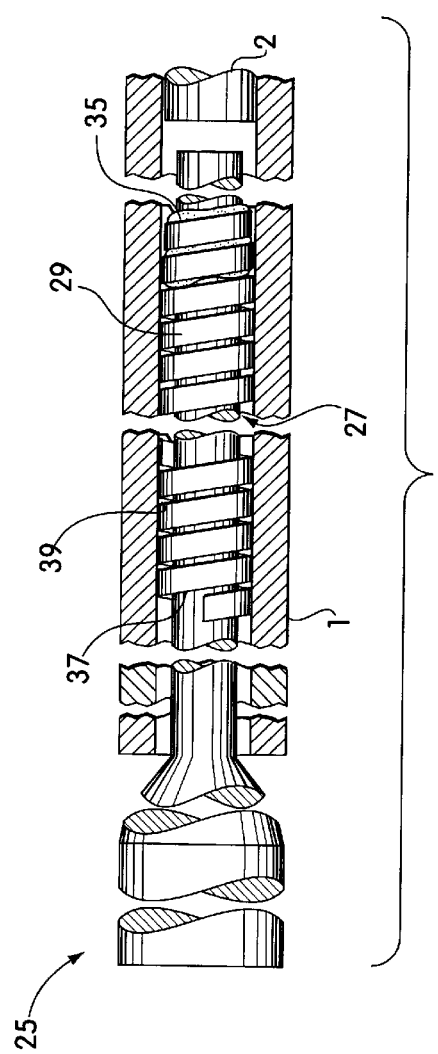
Fig. 4
Fig. 5

MEDICAL BACKLOADING WIRE

FIELD OF THE INVENTION

This invention relates to medical guidewires and to improved methods and devices to facilitate procedures involving their use.

BACKGROUND OF THE INVENTION

Guidewires are commonly used to guide and place catheters at a specific location in a patient's artery. The guidewire is receivable within a lumen of the catheter so that once the wire is positioned, the catheter then can be advanced over the wire and guided to the intended arterial location. Often during a catheterization procedure, it is necessary for the physician to use different catheters in treating a particular vessel. For example, in dilatation procedures it may be desirable to use a series of catheters having different balloon configurations and sizes. When using a series of catheters, it is important for the physician to be able to deliver each succeeding catheter to the same area quickly in order to reduce the time of the procedure and patient trauma. This is best accomplished by maintaining the indwelling guidewire in position while exchanging the catheters over it.

Rapid exchange or "monorail" catheters facilitate maintaining wire position in catheterization procedures where catheter exchanges are performed. These catheters have a short guidewire lumen located at the distal end of the catheter rather than through the full length of the catheter. Since the guidewire is not captivated through the entire length of the catheter, the portion of the wire that is outside of the patient will not be fully covered by the exiting catheter and can be grasped by the physician to maintain the position of the wire during the exchange.

During an exchange using rapid exchange catheters, a first, indwelling catheter is withdrawn proximally from the guidewire and a new catheter is backloaded onto the wire and advanced into the patient. Backloading involves inserting the proximal end of the guidewire, which remains outside the patient, into the distal port of the guidewire lumen at the distal end of the catheter then advancing the catheter distally over the wire. Though backloading the catheter allows the guidewire to remain in position within the patient during an exchange, the practice can be troublesome. The delicate tip of the catheter can be difficult to load over the proximal end of the guidewire and may become crushed and rendered useless during loading attempts.

Loading difficulties are not limited to rapid exchange catheters, as other types of angioplasty catheters may also be backloaded onto a guidewire. Before the guidewire is inserted into the patient, the physician may choose to load a catheter having a full length guidewire lumen by backloading the distal end of the catheter over the proximal end of the guidewire.

Two primary factors contribute to backloading difficulties. The tip of a coronary angioplasty catheter generally, and of a rapid exchange catheter in particular, is fragile and collapses easily if misaligned while being loaded onto a guidewire. The fragility results from the flexibility of the polymeric material from which the catheter tip is made and the thin wall of the tip. Commonly, a flexible catheter material such as high density polyethylene (HDPE) or nylon is chosen for the tip to reduce the risk of trauma to the patient as the catheter is advanced through a vessel. Efforts to reduce patient trauma by reducing the outside diameter of the catheter tip conflict with the desire to maintain controllability by using a stiffer, larger diameter guidewire. Maintaining a large guidewire lumen inside diameter that can receive the more controllable guidewires, while reducing outside diameter, leaves a very thin walled tip. By way of example, tip dimensions at the distal guidewire port may be on the order of 0.019" outside diameter and 0.016" inside diameter, leaving a wall thickness of only approximately 0.0015".

The problem of backloading such fragile tips is exacerbated by the relatively square profile of a hypotube connector located at the proximal end of some guidewires. The proximal end of the hypotube can snag the catheter tip during loading. Physicians are concerned with reducing procedure time and patient trauma and do not want to expend extra effort threading the catheter tip over the hypotube connector. If, during loading, a tip collapses upon itself or becomes crushed, the physician often discards the catheter and tries again with a new catheter rather than continuing to struggle with a damaged catheter.

It would be desirable to provide a simple, effective and inexpensive system and technique for facilitating the backloading of a medical catheter onto the proximal end of a medical guidewire. It is the general object of the present invention to provide such a system.

SUMMARY OF THE INVENTION

The backloading wire connects to the hypotube connector at the proximal end of a conventional guidewire to provide a gradual profile increase that facilitates backloading of the catheter. The backloading wire of the present invention is easily insertable into and removable from the hypotube connector by a physician grasping the wire with surgical gloved hands. Once installed into the hypotube connector, the exposed end of the backloading wire provides a tapered tip that is more easily inserted into the lumen of a catheter. The small diameter of the tip of the backloading wire is flexible and, therefore, less likely to damage the fragile distal tip of a catheter if the wire is not successfully navigated into the lumen on the first loading attempt. Once the catheter is fully loaded onto the guidewire, the backloading wire may be withdrawn from the hypotube connector and discarded, or left in place throughout the procedure.

A first embodiment of the backloading wire has double tapered tips and a central portion of a constant diameter. One end of the wire may be inserted into the hypotube connector of a guidewire where it will become temporarily frictionally engaged. The free end of the wire, also tapered, will be free to receive the distal tip of a catheter. Rather than tapering, the backloading wire may be coated with an insulation material at the free end only. The uncoated end of the wire has a reduced diameter to be inserted into the inside of the hypotube and the coated free end of the wire has a slightly increased diameter to provide a smooth transition for an oncoming catheter to slide over the hypotube.

A second embodiment of the backloading wire has a constant diameter. One end of the wire is formed into a wave shape to increase its effective diameter sufficiently so that it will frictionally engage the inside of the hypotube connector when inserted. The other end of the backloading wire, that will remain outside the hypotube, is straight and may have a rounded tip to facilitate insertion into the lumen of the catheter.

A third embodiment of the backloading wire has a tapered proximal segment and a helical coil secured to the distal segment of the wire. The coil is preferably formed from a rectangular cross-section wire. The distal end of the coil is attached to the backloading wire shaft while the proximal end of the coil is free to stretch and contract about the shaft. When the distal segment of the backloading wire is inserted into the hypotube connector of a guidewire, the helical coil stretches, reducing in diameter, thereby permitting insertion into the hypotube. Once inserted, the backloading wire self-locks in the hypotube connector. Axial separation forces cause the helical spring to contract and its diameter to expand to engage the inside of the hypotube. The backloading wire may be disconnected from the hypotube by twisting and simultaneously withdrawing the backloading wire from the hypotube. The twisting motion frees the locking engagement of the helical coil with the inside of the hypotube. Alternatively, the backloading wire may be made to be detachable by gripping and pulling the exposed proximal end of the helical coil. As with the second embodiment, the proximal segment of the backloading wire will remain free, outside the hypotube so that it may be inserted into the catheter.

The backloading, wire may be fabricated from stainless steel, or, to improve flexibility, it may be fabricated from a superelastic material such as nitinol. Alternatively, the backloading wire may be molded from a glass filled plastic composite material.

It is among the general objects of this invention to provide a backloading wire and method that will facilitate the backloading of a medical catheter onto a conventional guidewire.

It is another object of the invention to provide a backloading wire that is easily insertable into and removable from a hypotube connector at the proximal end of a conventional guidewire.

DESCRIPTION OF THE DRAWINGS

The foregoing and other objects and advantages of the invention will be appreciated more fully from the following further description thereof, with reference to the accompanying drawings wherein:

FIG. 4 is a fragmented diagram of an embodiment of the backloading wire having a helical coil at its distal end and a tapered proximal end.

FIG. 5 is an illustration of the distal end of the backloading wire having a helical coil engaged in the hypotube connector of a guidewire.

DESCRIPTION OF THE ILLUSTRATIVE EMBODIMENTS

Figure 1:
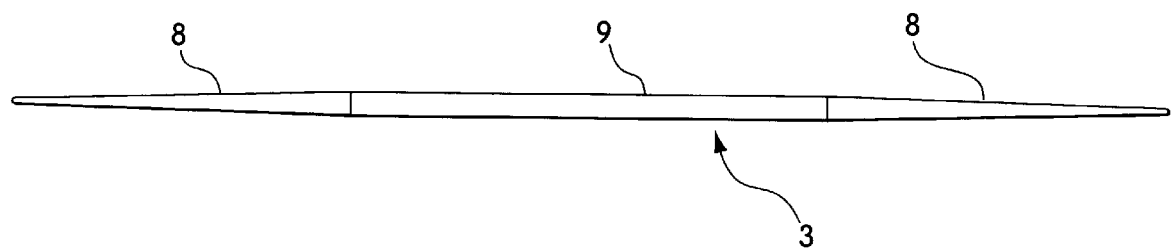
FIG. 1 is a diagram of an embodiment of the backloading wire having double tapered tips.

The first embodiment of the backloading wire 3, shown in FIG. 1, measures approximately 5–14 centimeters in length. The center portion of the wire 9 has a uniform diameter of approximately 0.014" and may be 1–10 centimeters in length. The tapered segments 8 at each end have a diameter decreasing from approximately 0.014" to 0.007" over about a two centimeter length. The backloading wire may be made from material commonly used for medical guidewires such as stainless steel. The taper at the ends may be created by grinding. Alternatively, rather than tapering by grinding, the wire may be coated to increase the diameter of the free end of the wire and uncoated at the opposite end to allow for its insertion into the hypotube. The slightly increased diameter of the coated end helps provide a smooth transition to the increased diameter of the hypotube connector for the advancing catheter.

Figure 2:
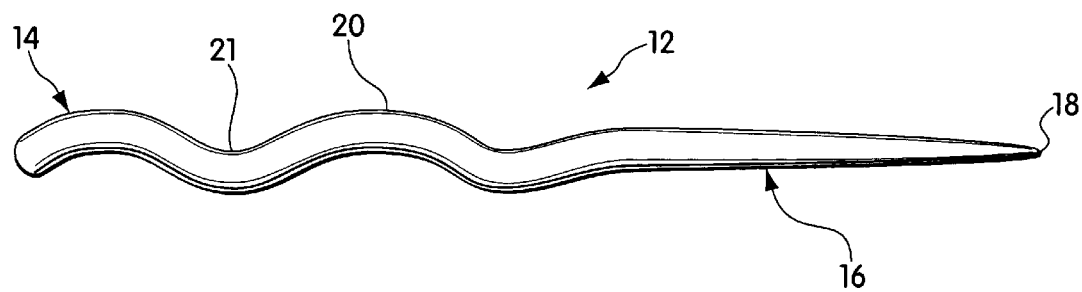
FIG. 2 is a diagram of an embodiment of the backloading wire having a straight end and a wave shaped end for insertion into a hypotube connector.

A second embodiment of the backloading wire is shown at 12 in FIG. 2. The wire may be made from a resilient material such as superelastic nitinol wire approximately 0.008" in diameter. The overall length of the wire is approximately 5 centimeters. The distal end of the wire 14 is distorted into a wave shape to frictionally engage the inside of a hypotube connector and the proximal end of the wire 16 is straight. The straight proximal end 16 may have a slightly rounded tip 18, to smoothly accept the guidewire lumen of a catheter.

The wave shape distortion encompasses about half the length (approximately 2.5 cm) of the total length of the wire. The waveform may be a two dimensional, zig-zag shape or may be a three dimensional, spiral shape created by wrapping the wire around a mandrel so that it becomes plastically deformed. The overall effective diameter of the distorted portion (measured from peak 20 to trough 21 of the waveform) may measure approximately 0.015" and should provide an interference fit with the inside diameter of a hypotube connector. As the wave portion is inserted into the hypotube, the wave shape will elastically deform slightly as surfaces engage. The wave shape provides secure frictional engagement with the hypotube, yet avoids a leak tight fit with the hypotube, thereby allowing the sterilization process to reach the inside of the hypotube if packaged in assembled form with the guidewire.

The interference fit between the wave shape tip and hypotube connector should be tight enough to prevent inadvertent dislodging, yet loose enough to allow disengagement with gloved hands. A pulling force of 0.04–0.2 lbs. to remove the backloading wire has been shown to provide adequate engagement. The surface of the wire may be oxidized to darken the color so as to make it visually distinguishable from the guidewire.

Figure 3:
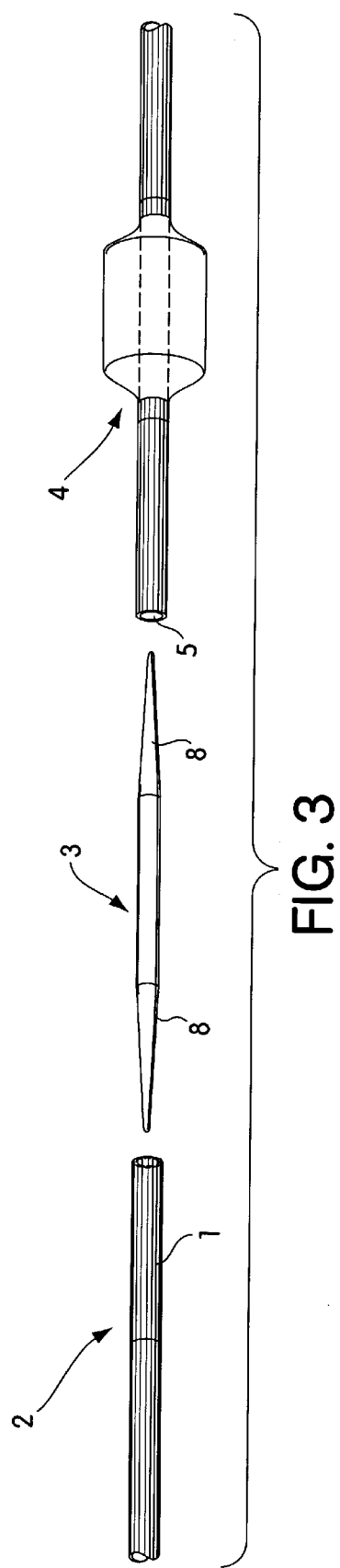
FIG. 3 is a schematic of a typical guidewire with a hypotube connector in position to receive the backloading wire and the distal end of a catheter.

Referring to FIG. 3, to use the backloading wire, either tapered end 8 (first embodiment), the wave shaped distal end 14 (second embodiment) is engaged within a hypotube connector 1 at the proximal end of a guidewire 2. The free end of the backloading wire receives the distal end of a catheter 4 to be backloaded onto the guidewire. The free end of the backloading wire presents a reduced profile, compared to that of an open hypotube connector, facilitating alignment with and entry into the small guidewire lumen 5 of a catheter 4. After the catheter has been loaded onto the guidewire, the backloading wire may be left in place throughout the procedure or removed from the hypotube connector to allow for connection of a full length extension wire.

FIG. 4 is a fragmented illustration of the third embodiment of the backloading wire shown generally at 25. A description of the wire connection system employed at the distal end of this backloading wire embodiment may be found in U.S. Pat. 5,133,364 (Palermo et al.), the disclosure of which is hereby incorporated by reference herein, in its entirety. The overall length of the backloading wire may be of the order of 12 centimeters. The wire may be fabricated from material commonly used for guidewires such as stainless steel. The backloading wire has a distal segment 27 of reduced diameter that holds a helical coil 29 that will engage the hypotube connector of the guidewire. Proximal to the distal segment, the diameter of the wire increases stepwise to a maximum diameter of approximately 0.014" at a central portion 31 of the wire. The central portion remains outside the hypotube connector during engagement and should have a comparable diameter to that of the guidewire shaft to provide a smooth transition between the wires.

The proximal segment of the backloading wire 33 tapers down from the maximum diameter of the central portion to a reduced diameter for easy insertion into the distal end of the catheter. By way of example, the tapered proximal segment may measure approximately 2 centimeters in length, tapering from a diameter of approximately 0.014" near the central portion 31 to a diameter of approximately 0.007". The central portion 31 (identified as segment A in FIG. 4) may span a length of approximately one centimeter. The tapered segment B may be about 0.5 centimeters long and may taper down to about 0.0055" diameter. The tapered segment B merges distally into constant diameter segment C which is approximately 0.0055" in diameter and about 1.5 centimeters in length.

Mounted on the distal segment 27 (segment C) is helical coil 29 having a relaxed inner diameter slightly greater (about 0.001" to 0.002") than the diameter of the distal segment. The coil has a relaxed outer diameter that is equal to or just slightly greater than the inner diameter of the hypotube connector to provide a light interference fit. By way of example, the coil 29 may be approximately 0.7 centimeter long and may have an outer diameter of 0.009" and an inner diameter of 0.007". The coil preferably is wound from wire that is of generally flat rectangular cross-sectional configuration, preferably of the order of 0.001" by 0.005". It is preferred to form the coil so that it is of somewhat tapering diameter with a slightly larger diameter provided at several of the turns of the proximal end of the coil to assure a slight interference fit (of the order of 0.001" to 0.002" in diameter) between the coil and the inner surface of the hypotube. For example, two or three turns at the proximal end of the coil 37 may be of a slightly enlarged outer diameter, of the order of 0.010"–0.011". The coil 29 is attached at its distal end to the distal segment of the backloading wire by brazing 35. The proximal end of the coil 37 is free to permit the coil to stretch as well as constrict about the distal segment 27. Preferably the coil 29 is of a length and is positioned so that the free proximal end 37 of the coil is not substantially more than 1.0 centimeter away from the distal tip 40 of the backloading wire.

Referring to FIG. 5, the backloading wire 25 is joined to a guidewire 2 by inserting the distal end of the backloading wire 27 into the hypotube connector 1 at the proximal end of the guidewire 2. During such insertion, at least some of the turns of the coil 29 engage, in light interference, the interior surface of the hypotube 1 to cause the coil to stretch longitudinally. The stretching of the coil 29 causes its diameter to constrict, thereby enabling the coil to be inserted into the hypotube 1. Once inserted, the coil 29 remains biased toward its expanded configuration causing the coil to bear against the interior surface of the hypotube 1. The rectangular cross-section of the wire from which the coil 29 is formed defines relatively sharp, distinct edges 39 which may engage with the interior surface of the hypotube 1 to provide a relatively firm connection that is resistant to axial separation. Thus, the arrangement is self-latching and requires no other manipulation to make the connection.

The backloading wire 25 and guidewire 1 may be detached by applying an axial separation force while simultaneously twisting the backloading wire in a direction that will tend to constrict the coil 29 about the distal segment 27 of the backloading wire. Thus, in the illustrative embodiment, the backloading wire 25 would be twisted clockwise, as seen from the left in FIG. 5, while withdrawing it axially from the hypotube 1. The backloading wire may be reconnected and disconnected from the hypotube as many times as needed. Alternatively, the helical coil 29 can be made a sufficient length so as to protrude beyond the end of the hypotube 1 while the distal segment 27 of the backloading wire is fully engaged. Rather than twisting and pulling the backloading wire 25 for removal, the user would simply grip the exposed proximal segment of the coil and pull it in a proximal direction to stretch the spring, reducing its diameter, and allow removal of the backloading wire from the hypotube 1.

From the foregoing it will be appreciated that a simpler and more effective method and apparatus for backloading a medical catheter onto a guidewire has been presented. The backloading wire embodiments described above will allow a physician to install the more flexible distal portion of a catheter over the proximal end of a guidewire equipped with a hypotube connector. Once the catheter has been fully loaded onto the guidewire, the backloading wire may be left in place throughout the procedure, or removed from the hypotube connector to be reinserted later or discarded.

It should be understood that the foregoing description of the invention is intended merely to be illustrative thereof and that other embodiments, modifications and equivalents may be apparent to those skilled in the art without departing from its spirit and principles.

Having thus described the invention, what we desire to claim and secure by Letters Patent is:

1. A backloading wire for backloading a medical catheter onto a medical guidewire, each of the catheter and guidewire having defined lengths, the backloading wire comprising:
   a wire substantially shorter than each of said defined lengths;
   a central portion having a defined diameter;
   a first end having a diameter that tapers from the diameter of the central portion to a reduced diameter;
   a second end having a diameter that tapers from the diameter of the central portion to a reduced diameter.

2. The backloading wire of claim 1 wherein the wire comprises stainless steel.

3. The backloading wire of claim 1 wherein the wire comprises a molded plastic composite.

4. The backloading wire of claim 1 wherein an insulating material covers the central portion and either the first end or the second end of the wire.

5. The backloading wire of claim 1 wherein the wire comprises a superelastic alloy.

6. The backloading wire of claim 5 wherein the superelastic alloy comprises a nickel-titanium composition.

7. The backloading wire of claim 1 wherein the diameter of at least a portion of the first end is approximately equivalent to the inside diameter of a hypotube connector at the end of a conventional guidewire so that the first and the diameter of the second end is sufficiently small to be receivable within a lumen of a catheter.

8. The backloading wire of claim 1 wherein the first and second ends have equivalent dimensions.

9. A backloading wire for backloading a medical catheter onto a medical guidewire, each of the catheter and guidewire having defined lengths, the backloading wire comprising:
   a wire substantially shorter than each of said defined lengths;
   a first portion having a defined diameter;
   a second portion having a free end with sufficient flexibility and being dimensioned to be inserted into the distal end of the medical catheter without damaging the tip of the catheter.

10. The backloading wire of claim 9 wherein the wire comprises stainless steel.

11. The backloading wire of claim 9 wherein the wire comprises a molded plastic composite.

12. The backloading wire of claim 9 wherein an insulating material covers the central portion and either the first end or the second end of the wire.

13. The backloading wire of claim 9 wherein the wire comprises a superelastic alloy.

14. The backloading wire of claim 13 wherein the superelastic alloy comprises a nickel-titanium composition.

15. A backloading wire for backloading a medical catheter onto a medical guidewire, each of the catheter and guidewire having defined lengths, the backloading wire comprising:

a wire substantially shorter than each of said defined lengths;

a first end that is substantially straight and a second end having a wave form shape capable of being frictionally engaged within a hypotube connector of a medical guidewire.

16. The backloading wire of claim 15 wherein the wave form shape of the second end is two-dimensional.

17. The backloading wire of claim 15 wherein the wave form shape of the second end is a three-dimensional spiral shape.

18. The backloading wire of claim 15 wherein the wire comprises stainless steel.

19. The backloading wire of claim 15 wherein the wire comprises a molded plastic composite.

20. The backloading wire of claim 15 wherein an insulating material covers the central portion and either the first end or the second end of the wire.

21. The backloading wire of claim 15 wherein the material of the wire is a superelastic alloy.

22. The backloading wire of claim 21 wherein the superelastic alloy comprises a nickel-titanium composition.

23. A backloading wire for backloading a medical catheter onto a medical guidewire, each of the catheter and guidewire having defined lengths, the backloading wire comprising:

a wire substantially shorter than each of said defined lengths;

a proximal segment that tapers from a first diameter to a reduced diameter;

a distal segment that tapers from a first diameter to a reduced diameter and;

a helical coil spring positioned on and affixed to the distal segment of the wire.

24. The backloading wire of claim 23 wherein the wire comprises stainless steel.

25. The backloading wire of claim 23 wherein the wire comprises molded plastic composite.

26. The backloading wire of claim 23 wherein an insulating material covers the central portion and either the first end or the second end of the wire.

27. The backloading wire of claim 23 wherein the wire comprises a superelastic alloy.

28. The backloading wire of claim 27 wherein the superelastic alloy comprises a nickel-titanium composition.

29. A backloading wire system comprising:

a medical guidewire having a hypotube connector at its proximal end and a backloading wire, shorter than the guidewire, having a first end adapted to become engaged within the hypotube connector and a second end dimensioned and adapted to be insertable into the distal end of a lumen of a medical catheter.

30. A method of backloading a medical catheter having a defined length onto a guidewire having a defined length and having a hypotube connector comprising:

providing a backloading wire substantially shorter than each of the defined lengths of the catheter and the guidewire and having one end adapted to be inserted into and to become engaged with the hypotube connector and having a second end adapted to receive a lumen of the medical catheter;

inserting the first end of the backloading wire into the hypotube connector of the guidewire;

inserting the second end of the backloading wire into the distal end of the medical catheter;

advancing the medical catheter distally over the guidewire.

31. A method of performing a catheter exchange over an indwelling guidewire having a defined length with a rapid exchange catheter having a defined length comprising:

providing a short wire substantially shorter than each of the defined lengths of the catheter and the guidewire having one end insertable into a socket and the other end having a reduced diameter;

inserting the short wire into a hypotube;

withdrawing the indwelling rapid exchange catheter;

backloading a new rapid exchange catheter onto the short wire.

32. A backloading wire as defined in any one of claims 1, 9, 15, 23 or 29 wherein the wire has a length of approximately 5–14 centimeters.

* * * * *